(12) United States Patent
Williams

(10) Patent No.: US 10,786,493 B2
(45) Date of Patent: *Sep. 29, 2020

(54) METHOD OF TREATING VIRAL INFECTIONS

(71) Applicant: MyMD Pharmaceuticals, Inc., Tampa, FL (US)

(72) Inventor: Jonnie R. Williams, Sarasota, FL (US)

(73) Assignee: MyMD Pharmaceuticals, Inc., Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/791,290

(22) Filed: Feb. 14, 2020

(65) Prior Publication Data

US 2020/0179366 A1 Jun. 11, 2020

Related U.S. Application Data

(62) Division of application No. 15/558,094, filed as application No. PCT/US2016/025126 on Mar. 31, 2016, now Pat. No. 10,588,899.

(60) Provisional application No. 62/140,618, filed on Mar. 31, 2015.

(51) Int. Cl.
| | |
|---|---|
| *A61K 31/465* | (2006.01) |
| *A61P 31/22* | (2006.01) |
| *A61P 31/18* | (2006.01) |
| *A61P 31/16* | (2006.01) |
| *A61P 3/08* | (2006.01) |
| *A61K 31/4439* | (2006.01) |
| *A61K 8/49* | (2006.01) |
| *C07K 14/47* | (2006.01) |

(52) U.S. Cl.
CPC .......... *A61K 31/465* (2013.01); *A61K 8/4926* (2013.01); *A61K 31/4439* (2013.01); *A61P 3/08* (2018.01); *C07K 14/4747* (2013.01); *Y02A 50/30* (2018.01)

(58) Field of Classification Search
CPC ................ A61K 31/465; A61P 31/12–22
See application file for complete search history.

(56) References Cited

U.S. PATENT DOCUMENTS

| | | | |
|---|---|---|---|
| 5,276,043 | A | 1/1994 | Lippiello et al. |
| 7,090,648 | B2 | 8/2006 | Sackner et al. |
| 8,916,596 | B2 | 12/2014 | Kristie et al. |
| 9,884,055 | B2 | 2/2018 | Williams |
| 10,314,775 | B2 | 6/2019 | Williams |
| 10,471,052 | B2 | 11/2019 | Williams |
| 10,517,856 | B2 | 12/2019 | Williams |
| 2008/0188527 | A1 | 8/2008 | Cashman |

FOREIGN PATENT DOCUMENTS

| | | |
|---|---|---|
| JP | 2002-516869 A | 6/2002 |
| WO | 2013016580 A2 | 1/2013 |
| WO | 2016/081369 A2 | 5/2016 |
| WO | 2016/161051 A1 | 10/2016 |
| WO | 2016/161055 A2 | 10/2016 |

OTHER PUBLICATIONS

Akalin, M. K. et al., "Pyrolysis of tobacco reside: Part 1. Thermal", BioResources, 2011, vol. 6, No. 2, pp. 1520-1531.
Poehlmann et al., "Repeated H2O2 exposure drives cell cycle progression in an in vitro model of ulcerative colitis," J Cell Mol. Med. Dec. 2013; 17 (12):1619-1631.
Sep. 27, 2016—International Search Report and Written Opinion—PCT/US2016/025126.
Campos, P.J. et al., "Simple and versatile synthesis of 1-pyrroline derivative through thermal rearrangement of N-Cyclopropylimines", Thetrahedron Letters, 2002, vol. 43, No. 49, pp. 8811-8813.
Marriner, G. A. et al., "An improved synthesis of (+)-N'-nitrosonornicotine 5'-acetate", The Journal of Organic Chemistry 2009, vol. 74, No. 7, pp. 2891-2892.
Knorr, A. et al., "Computer-Assisted Structure Identification (CASI)—An Automated Platform for High-Throughput Identification of Small Molecules by Two-Dimensional Gas Chromatography Couples to Mass Spectrometry", Analytical Chemistry, 2013, vol. 85, No. 23, pp. 11216-11224.
May 22, 2015—Khor et al. "The kinase DYRK1A reciprocally regulates the differentiation of Th17 and regulatory T cells"—Ed. Arup K Chakraborty. eLife_e05920.
Jan. 30, 2015—Fernandez-Martinez P, et al. "DYRK1A: the double-edged kinase as a protagonist in cell growth and tunorigenesis"—Molecular & Cellular Oncology vol. 2, 2015 Issue 1.
Dec. 7, 2015—Booiman et al.,"DYRK1A Controls HIV-1 Replication at a Transcriptional Level in a NEAT Dependent Manner"—PLOS One.
May 14, 2014—Helen Dodson, "Yale Researches Identify Gene that Causes Obesity-related Metabolic Syndrome"—Yale News.
Oct. 2013—Msolly et al., Hydrogen Peroxide: an Oxidant Stress Indicator in Type 2 Diabetes Mellitus—Journal of Cardiovascular Disease vol. 1. No. 2.
Sep. 13, 2001—Jobsis et al., "Hydrogen peroxide in breath condensate during a common cold"—Mediators of Inflammation, vol. 10, 351-354.
Oct. 2001—Goth et al., "Blood Catalase Deficiency and Diabetes in Hungary"—Diabetes Care vol. 24, No. 10, 1839-1850.
Dec. 2014—Olagnier et al., "Cellular Oxidative Stress Response Controls the Antiviral and Apoptotic Programs in Dengue Virus-Infected Dendritic Cells"—PLOS Pathogens vol. 10 Issue 12.
Jun. 24, 2014—Jurk et al., "Chronic inflammation induces telomere dysfunction and accelerates age in mice"—Nature Communications.
2004—Sharifi et al., "Serum ferritin in type 2 diabetes mellitus and its relationship with HbA1c"—Acta Medica Iranica vol. 42. No. 2 pp. 142-145.

(Continued)

*Primary Examiner* — Theodore R. West
(74) *Attorney, Agent, or Firm* — Banner & Witcoff, Ltd.

(57) ABSTRACT

In one aspect, a method of treating a disorder associated with chronic inflammation includes administering to an individual in need thereof a therapeutically effective amount of isomyosmine or a pharmaceutically acceptable salt thereof. In some aspects, the disorder is a cancer, an autoimmune disorder, hypertension, or autism. In other aspects, isomyosmine is administered to treat viral infections or disorders associated with elevated levels of hydrogen peroxide and/or other Reactive Oxygen Species (ROS).

20 Claims, 1 Drawing Sheet

(56) References Cited

OTHER PUBLICATIONS

2016—Gammella et al., "Dual Role of ROS as Signal and Stress Agents: Iron Tips the Balance in favor of Toxic Effects"—Oxidative Medicine and Cellular Longevity vol. 2016 Artile ID 8629024 p. 1-9.
2009—Reardon et al., "Iron injections in mice increase skeletal muscle iron contenct, induce oxidative stress and reduce exercise preformance" Experimental Physiology 94.6 pp. 720-730.
2015—Maheshwari et al., "Correlation between serum ferritin and glycaemic control in patients of type 2 diabetes mellitus: a case control study"—Int J. Res. Med. Sci. Sep. 3(9) pp. 2327-2330.
Dec. 17, 2013—Dixon et al., "The role of iron and reactive oxygen species in cell death"—Nature Chemical Biology vol. 10.
Mar. 25, 2010—Wallace "Telomere Diseases"—The New England Journal of Medicine 362;15.
Johns Hopkins Medicine—"Telomere Syndromes and Dyskeratosis Congenita" as retraced on Apr. 30, 2017.
Oct. 2010—Kuhlow et al., "Telomerase deficiency impairs glucose metabolism and insulin secretion"—Aging vol. 2. No. 10.
2013—Anchelin et al,. "Premature aging in telomerase-deficient zebrafish"—Disease Models & Mechanisms 6, pp. 1101-1112.
2014—Gordon, "Reactive Oxygen Species and Telomere Dysfunction: Investigating the Underlying Mechanisms of Aging and Related Diseases"—Disseration at University of NC at Chapel Hill—Department of Chemistry.
2006 Spring Rejuvenation Res. 9(1): 61-3 Flanary BE et al., "Analysis of telomere length and telomerase activity in tree species of various lifespans, and with age in the bristlecone pine *Pinus longaeva*".
Dec. 2008—Tsukimori et al., "Serum Uric Acid Levels Correlate With Plasma Hydrogen Peroxide and Protein Carbonyl Levels in Preeclampsia"—American Journal of Hypertension vol. 21. No. 12 pp. 1343-1346.
Jun. 2014—Ellervik et al., "Need for Reclassification of Diabetes Secondary to Iron Overload in the ADA and WHO Classifcations"—Diabetes Care vol. 37 pp. e137-e138.
Jul. 11, 2016—Petimani et al., "Correlation between serum uric acid, nitric oxide, ferritn and HbA1c levels in Type II diabetic patients"—Journal of Investigational Biochemistry.
Jan. 17, 2017—Anderson, "Brian Iron May Predict Progression in Alzheimer's"—Medscape 2017.
PubMed Central, Figure 1: Annu Rev Genomics Hum Genet. 2009; 10: 45—https://www.ncbi.nlm.nih.gov/pmc/articles/PMC2818564/figure/F1/?report=objectonly—Retrieved on Aug. 2, 2017.
Apr. 17, 2017—Karidis, "Diabetes is even deadlier than we thought, study suggests"—Washington Post: Health & Science—https://www.washingtonpost.com/national/health-science/diabetes-is-even-deadlier-than-we-thought-study-suggests/2017/04/07/28689b94-faca-11e6-be05-1a3817ac21a5_story.html?utm_term=.1a4936fdbf18—Retrieved on Sep. 13, 2017.
Jan. 30, 2014—Rachdi et al., "Dyrk1a haploinsufficiency induces diabetes in mice through decreased pancreatic beta cell mass"—Diabetologia vol. 57, Issue 5, pp. 960-969.
Ria Susan George, Nandini Manjunath, Manjunath B. V., and Kishore Bhat, "Estimation of serum cortisol levels and its correlation with salivary cortisol levels in coronary artery disease patients with and without periodontitis: a cross sectional study," Int. J. Res. Med. Sci. May 2017; 5(5): 1930-1935; www.msjonline.org (pISSN 2320-6071 ? eISSN 2320-6012).
Chang Xia, Xiaoquan Rao, and Jixin Zhong, "Review Article—Role of T Lymphocytes in Type 2 Diabetes and Diabetes-Associated Inflammation," Hindawi, Journal of Diabetes Research, vol. 2017, Article ID 6494795, 6 pages (https://doi.org/10.1155/2017/6494795).
Fasching et al., "Hypoglycemic action of tricyclic antidepressant desmethylimipramine, but not of monoamine oxidase-inhibitor moclobemide in healthy men—possible implications for diabetes thereapy," Diabetologia, 38 (Suppl. 1), pp. A205 1995.
Harris, Sarah E., Martin-Ruiz, Carmen, von Zglinicki, Thomas, Starr, John M., and Deary, Ian J., "Telomere length and aging biomarkers in 70-year-olds: the Lothian Birth Cohort 1936," Neurobiology of Aging 33 (2012) 1486.e3-1486.e8 (6 pages).
Schäfer, Stefan, and Kolkhof, Peter, "Failure is an option: learning from unsuccessful proof-of-concept trials," Drug Discovery Today, vol. 13, Nos. 21/22 (Nov. 2008), pp. 913-916.
Verma, Suman, Tachtatzis, Phaedra, Penrhyn-Lowe, Sue, Scarpini, Cinzia, Jurk, Diana, Von Zglinicki, Thomas, Coleman, Nick, and Alexander, Graeme J. M., "Sustained Telomere Length in Hepatocytes and Cholangiocytes with Increasing Age in Normal Liver," Hepatology, vol. 56, No. 4, (2012), pp. 1510-1520.
Renault, Valérie, Thorne, Lars-Eric, Eriksson, Per-Olof, Butler-Browne, Gillian, and Mouly, Vincent, "Regenerative potential of human skeletal muscle during aging," Aging Cell (2002) 1, pp. 132-139.
Hörig, Heidi and Pullman, William, "Review, From bench to clinic and back: Perspective on the 1st IQPC Translational Research conference," Journal of Translational Medicine 2004, 2:44, pp. 1-8.
Meier, Karen and Nanney, Lillian B., "Emerging new drugs for wound repair," Expert Opinion on Emerging Drugs, 11 (1), pp. 23-37, 2006.
PubChem, SID 254779196 (Nov. 11, 2015) URL: http://pubchem.ncbi.nlm.nih.gov/substance/254779196.
Oct. 19, 2018—EP Search Report—EP App No. 16774156.0.
Dec. 1, 1960—Maxwell et al., "Monoamine Oxidase Inhibitors in Hypertension" American Journal of Cardiology, vol. 6, No. 6, p. 1146-1151.
Jul. 24, 2013—Lee et al., "Effects of monoamine oxidase inhibitors pargyline and tranylcypromine on cellular proliferation in human prostate cancer cells" Oncology Reports, vol. 30, No. 4, p. 1587-1592.
Nov. 7, 1964—Wickström et al., "Treatment of diabetics with monoamine-oxidase inhibitors" The Lancet, p. 995-997.
Fedarko, PhD, Neal S., "The Biology of Aging and Frailty," NIH Public Access, Clin Geriatr Med. Feb. 2011; 27(1): 27-37. doi:10.1016/j.cger.2010.08.006.
Maekawa, Toshio; Liu, Binbin; Nakai, Daisuke; Yoshida, Keisuke; Nakamura, Ken-ichi; Yasukawa, Mami; Koike, Manabu; Takubo, Kaiyo; Chatton, Bruno; Ishikawa, Fuyuki; Masutomi, Kenkichi; and Ishii, Shunsuke, "ATF7 mediates TNF-?-induced telomere shortening," Nucleic Acids Research, 2018; doi: 10.1093/narlgky155 (18 pgs).
Cosorich, Ilaria; Dalla-Costa, Gloria; Sorini, Chiara; Ferrarese, Roberto; Messina, Maria Josè; Dolpady, Jayashree; Radice, Elisa; Mariani, Alberto; Testoni, Piere Alberto; Canducci, Filippo; Comi, Giancarlo; Martinelli, Vittorio; and Falcone, Marika, "High frequency of intestinal TH17 cells correlates with microbiota alterations and disease activity in multiple sclerosis," Science Advances ? Research Article, Health and Medicine, Sci. Adv. 2017: 3:e1700492 (Jul. 12, 2017) 9 pages.
Yang, Fang; Li, Bingmei; Li, Li; and Zhang, Hongwei, "The clinical significance of the imbalance of Th17 and Treg cells and their related cytokines in peripheral blood of Parkinson's disease patients," Int. J. Clin. Exp. Med. 2016: 9 (9):17946-17951.
Colgate Virology (and Immunology) Blog: Th17 Cells Play a Role in Alzheimer's Disease, Sunday, Nov. 3, 2013 (3 pages).
Taleb, Soraya; Tedgui, Alain; and Mallat, Ziad, "IL-17 and Th17 Cells in Atherosclerosis, Subtle and Contextual Roles," Arterioscler Thromb Vasc Biol is available at http://atvb.ahajournals.org DOI:10.1161/ATVBAHA.114.303567 pp. 258-265.
Littman, Dan and Huh, Jun, "Exploring the role of Th17-inducing maternal intestinal bacteria in autism," https://www.sfari.org/funded-project/exploring-the-role-of-th17-inducing-maternal-intestinal-bacteria-in-autism (printed Dec. 10, 2017).
Marshall, Erin A.; Ng, Kevin W.; Kung, Sonia H.Y.; Conway, Emma M.; Martinez, Victor D.; Halvorsen, Elizabeth C.; Rowbotham, David A.; Vucic, Emily A.; Plumb, Adam W.; Becker-Santos, Daiana D.; Enfield, Katey S. S.; Kennett, Jennifer Y.; Bennewith, Kevin L.; Lockwood, William W.; Lam, Stephen; English, John C.; Abraham, Ninan; and Lam, Wan L. "Emerging roles of T helper 17 and regulator T cells in lung cancer progression and metastasis," Molecular Cancer (2016) 15:67 DOI 10.1186/s12943-016-0551-1 (15 pgs).

(56) References Cited

OTHER PUBLICATIONS

Pomié, Céline; Garidou, Lucile; and Burcelin, Rémy, "Intestinal ROR?t-generated Th17 cells control type 2 diabetes: A first antidiabetic target identified from the host to microbiota crosstalk," Inflammation & Cell Signaling 2016; 3: e1074. doi: 10.14800/ics. 1074; © 2016 http://www.smartscitech.com/index.php/ics (7 pages).

Jose, Shyam Sushama; Bendickova, Kamila; Kepak, Tomas; Krenova, Zdenka; and Fric, Jan, Chronic Inflammation in Immune Aging: Role of Pattern Recognition Receptor Crosstalk with the Telomere Complex?, Frontiers in Immunology, (www.frontiersin.org) Mini Review, published Sep. 4, 2017, vol. 8, Aerticle 1078, doi: 10.3389/fimmu.2017.01078 (10 pages).

WIPO, "Patent Expert Issues: Inventions in Space," 2 pages (http://www.wipo.int/patents/en/topics/outer_space.html), printed Nov. 16, 2017.

Tian, Ye; Ma, Xiaoli; Yang, Chaofei; Su, Peihong; Yin, Chong; and Qian, Al-Rong, "Review, The Impact of Oxidative Stress on the Bone System in Response to the Space Special Environment," International Journal of Molecular Sciences, Int. J. Mol. Sci. 2017, 18, 2132; doi:10.3390/ijms18102132, (www.mdpi.com/journal/ijms), 9 pages.

Volpe, Kristin Della, (commentary by Hackett, Ruth and Vicennati, Valentina), "High Evening Cortisol Levels Linked to Increased Risk for Type 2 Diabetes," endocrineweb, printed Sep. 23, 2017, 3 pages.

Wu, W., Liu, P., and Li, J., "Necroptosis: an emerging form of programmed cell death," Crit. Rev. Oncol. Hematol. Jun. 2012; 82(3):249-58. doi: 10.1016/j.critrevonc.2011.08.004.Epub Oct. 1, 2011.

Necroptosis—Wikipedia (https://en.wikipedia.org/wiki/Necroptosis) printed Sep. 24, 2019.

Rios, Ester C. S.; Szczesny, Bartosz; Soriano, Francisco G.; Olah, Gabor; and Szabo, Csaba, "Hydrogen sulfide attenuates cytokine production through the modulation of chromatin remodeling," International Journal of Molecular Medicine 35: 1741-1746, 2015 (DOI: 10.3892/ijmm.2015.2176).

Syrop, Jackie, Can Anti-TNF Therapies Treat Insulin Resistance and Type 2 Diabetes?, (Jan. 18, 2018) https://www.centerforbiosimilars.com/news/can-antitnf-therapies-treat-insulin-resistance-an . . . .

Chang, Rudy; Yee, Kei-Lwun; and Sumbria, Rachita K., Tumor necrosis factor ? Inhibition for Alzheimer's Disease, Journal of Central Nervous System Disease, vol. 9: 1-5; DOI: 10.1177/1179573517709278.

Brymer, Kyle J.; Romay-Tallon, Raquel; Allen, Josh; Caruncho, Hector J.; and Kalynchuk, Lisa E., Exploring the Potential Antidepressant Mechanisms of TNF? Antagonists, Frontiers in Neuroscience, Review, published Feb. 11, 2019; DOI: 10.3389/frins.2019. 00098; (www.frontiersin.org; vol. 13, Article 98).

Shefa, Ulfuara; Kim, Min-Sik; Jeong, Na Young; and Jung, Junyang, "Antioxidant and Cell-Signaling Functions of Hydrogen Sulfide in the Central Nervous System," Hidawi, Oxidative Medicine and Cellular Longevity, vol. 2018, Article ID 1873962, 17 pages, (https://doi.org/10.115/2018/1873962).

Gherasim, Carmen; Yadav, Pramod K.; Kabil, Omer; Niu, Wei-Ning; and Banerjee, Ruma, "Nitrite Reductase Activity and Inhibition of H2S Biogenesis by Human Cystathionine ?-Synthase," PLOS ONE ? www.plosone.org; Jan. 2014, vol. 9, issue 1, e85544 (7 pages).

H2S Platform, © 2016 Antibe Therapeutics, Inc.

The Economist, "Explaining Autism, Energy drain," The cause of autism may be faulty mitochondria, Dec. 2, 2010, 3 pages.

Chaaya, Rana; Alfarano, Chiara; Guilbeau-Frugier, Céline; Coatrieux, Christelle; Kesteman, Anne-Sylvie; Parini, Angelo; Fares, Nassim; Gue, Michelle; Schanstra, Joost P.; and Bascands, Jean-Loup, "Pargyline reduces renal damage associated with ischaemia-reperfusion and cyclosporin," Nephrol Dial Transplant (2010) pp. 1-10 (DOI: 10.1093/ndt/gfq445).

Milton Ng, "Role of hydrogen peroxide in the aetiology of Alzheimer's disease: implications for treatment." Drugs Aging. 2004:21(2):81-100 (http://www.ncbi.nlm.nih.gov/m/pubmed/14960126/, 2 pages.

Cohen, Gerald; Farooqui, Rafay; and Kelsler, Natasa, Parkinson disease: A new link between monoamine oxidase and mitochondrial electron flow, Proc. Natl. Acad. Sci. USA, vol. 94, pp. 4890-4894, May 1997, Biochemistry.

Cathcart, Martha K. and Bhattacharjee, Ashish, "Monoamine oxidase A (MAO-A): a signature marker of alternatively activated monocytes/macrophages," Inflammation & Cell Signaling 2014: 1: 3161 (http://www.smartscitech.com/index.php/ics (8 pages).

Wajant, Harald and Siegmund, Daniela, "TNFR1 and TNFR2 in the Control of the Life and Death Balance of Macrophages," Frontiers in Cell and Developmental Biology, Review; published May 29, 2019; DOI: 10.3389/fcell.2019.00091; www.frontiersin.org; vol. 7, article 91 (14 pages).

Dhuriya, Yogesh K. and Sharma, Divakar, "Necroptosis: a regulated inflammatory mode of cell death," Journal of Neuroinflammation (2018) 15:199 (https://doi.org/10.1186/s12974-018-1235-0) (9 pages).

Role of Hydrogen Peroxide in the Aetiology of Alzheimer's Disease, Drugs & Aging 21(2)—Feb. 2004; https://www.researchgate.net/publication/257898328 Role of Hydrogen Peroxide in th . . . , 11 pages.

Oct. 9, 2019—U.S. Notice of Allowance—U.S. Appl. No. 15/719,875.

Glenn, Justin D.; Pantoja, Itzy Morales; Caturegli, Patrizio; Whartenby, Katharine A.; "MYMD-1, a novel alkaloid compound, ameliorates the course of experimental autoimmune encephalomyelitis," Journal of Neuroimmunology, Short Communication, vol. 339, 577115, Feb. 15, 2020; https://www.jni-journal.com/article/S0165-5728(19)30220-6/fulltext (10 pages).

Oct. 3, 2019—PCT/U.S. Written Opinion—App 2018/050856.

Dec. 18, 2019—(JP) Notice of Reasons for Refusal—App 2017-550601—Eng Tran.

Akalm, Mehmet K. and Karagöz, Selhan, "Pyrolysis of Tobacco Residue: Part 1. Thermal," (2011), BioResources 6(2), pp. 1520-1531.

The Lancet, Preliminary Communication, (dated Nov. 7, 1964)—pp. 995-997.

Maxwell, M.D., Morton H.; Bernstein, M.D., Harold; Roth, M.D., Samuel; and Kleuman, M.D., Charles R., "Monoamine Oxidase Inhibitors in Hypertension," Oncology Reports (2013), vol. 30, No. 4, pp. 1587-1592.

Musgrave, Travis; Benson, Curtis; Wong, Grace; Browne, Ikennah; Tenorio, Gustavo; Rawu, Gail; Baker, Glen B.; and Kerr, Bradley J., The MAO inibitor phenelzine improves functional outcomes in mice with experimental autoimmune encephalomyelitis (EAE). Brain, Behavior, and Immunity (2011), vol. 25, Issue 8, pp. 1677-1688.

Lee, Hyung Tae; Chol, Mi Ran; Doh, Mi Sook; Jung, Kyoung Hwa; and Chai, Young Gyu, Effects of the monoamine oxidase inhibitors pargyline and tranylcypromine on cellular proliferation in human prostate cancer cells, The American Journal of Cardiology, 1960, vol. 6, No. 6, pp. 1146-1151.

Berge, Stephen M.; Bighley, Lyle D; and Monkhouse, Donald C., "Pharmaceutical Salts," Journal of Pharmaceutical Sciences, Jan. 1977, vol. 66, No. 1.

Haynes, Delia A.; Jones, William; and Motherwell, W.D. Samuel, "Occurrence of Pharmaceutically Acceptable Anions and Cations in the Cambridge Structural Database," Journal of Pharmaceutical Sciences, vol. 94, No. 10, Oct. 2005.

Paulekuhn, G. Steffen; Dressman, Jennifer B.; and Saal, Christoph, "Trends in Active Pharmaceutical Ingredient Salt Selection based on Analysis of the Orange Book Database," J. Med. Chem. 2007, 50, 6665-6672.

Gould, Philip L., "Salt selection for basic drugs," International Journal of Pharmaceutics, 33 (1986) 201-217.

Bastin, Richard J.; Bowker, Michael J.; and Slater, Bryan J., "Salt Selection and Optimisation Procedures for Pharmaceutical New Chemical Entities," Organic Process Research & Development 2000, 4, 427-435.

Liguori, Ilaria; Russo, Gennaro; Curcio, Francesco; Bulli, Giulia; Aran, Luisa; Della-Morte, David; Gargiulo, Gaetano; Testa, Gianluca; Cacciatore, Francesco; Bonaduce, Domenico; and Abete, Pasquale, "Oxidative stress, aging, and diseases," Clinical Interentions in Aging 2018:13 757-772.

(56) References Cited

OTHER PUBLICATIONS

To, Eunice E.; Erlich, Jonathan R.; Liong, Felicia; Luong, Raymond; Liong, Stella; Esaq, Farisha; Oseghale, Osezua; Anthony, Desiree; McQualter, Jonathan; Bozinovski, Steven; Vlahos, Ross; O'Leary, John J.; Brooks, Doug A.; and Selemidis, Stavros, "Mitochondrial Reactive Oxygen Species Contribute to Pathological Inflammation During Influenza A Virus Infection in Mice," Antioxidants & Redox Signaling, vol. 00, No. 00, 2019, Mary Ann Liebert, Inc. DOI: 10.1089/ars.2019.7727 (14 pages).

Bencherif, Merouane; Lippiello, Patrick M.; Lucas, Rudolf; and Marrero, Mario, B., "Alpha7 nicotinic receptors as novel therapeutic targets for inflammation-based diseases," Cell. Mol. Life Sci. (2011) 68:931-949.

METHOD OF TREATING VIRAL INFECTIONS

CROSS REFERENCE TO RELATED APPLICATION

This application is a division of U.S. application Ser. No. 15/558,094, filed Sep. 13, 2017, which is a U.S. National Phase of PCT/US16/25126, filed Mar. 31, 2016, which claims priority to U.S. provisional application No. 62/140,618, filed Mar. 31, 2015, the disclosure of which is hereby incorporated by reference in its entirety.

SUMMARY

In one aspect, a method of treating a cancer comprises administering to an individual in need thereof a pharmaceutical composition containing a therapeutically effective amount of isomyosmine or a pharmaceutically acceptable salt thereof. Aspects of treating cancers may involve the modification of a tumor microenvironment. It is believed that isomyosmine blocks the production or otherwise reduces the concentration of hydrogen peroxide and/or other Reactive Oxygen Species (ROS) in the microenvironment, which in turn may help restore normal function of endogenous species. Modification of the tumor microenvironment also may improve the efficacy other cancer therapies, e.g., chemotherapies. To the extent that the presence of hydrogen peroxide and/or other ROS may be responsible for oncogenesis, isomyosmine may also be effective for preventing or delaying the onset of a tumor.

In another aspect, a method of treating an autoimmune disorder comprises administering to an individual in need thereof a pharmaceutical composition containing a therapeutically effective amount of isomyosmine or a pharmaceutically acceptable salt thereof.

In another aspect, a method of treating autism comprises administering to an individual in need thereof a pharmaceutical composition containing a therapeutically effective amount of isomyosmine or a pharmaceutically acceptable salt thereof.

In another aspect, a method of treating a viral infection comprises administering to an individual in need thereof a pharmaceutical composition containing a therapeutically effective amount of isomyosmine or a pharmaceutically acceptable salt thereof. In one example, the virus is human immunodeficiency virus (HIV). In another example, the virus is human papillomavirus (HPV).

In another aspect, a method of treating hypertension or high blood pressure comprises administering to an individual in need thereof a pharmaceutical composition containing a therapeutically effective amount of isomyosmine or a pharmaceutically acceptable salt thereof.

In some aspects, a method of treating a disorder associated with chronic inflammation comprises administering to an individual in need thereof a pharmaceutical composition containing a therapeutically effective amount of isomyosmine or a pharmaceutically acceptable salt thereof.

In other aspects, a method of treating a disorder associated with increased levels of hydrogen peroxide and/or other ROS comprises administering to an individual in need thereof a pharmaceutical composition containing a therapeutically effective amount of isomyosmine or a pharmaceutically acceptable salt thereof. It is postulated that isomyosmine inhibits the production of hydrogen peroxide, either directly or indirectly, e.g., by inhibiting enzymes, such as monoamine oxidase, that produce hydrogen peroxide and/or other ROS. Disorders associated with increased levels of hydrogen peroxide and/or other ROS may include cancers, autoimmune disorders, and the like, including specific cancers and autoimmune disorders mentioned herein as well as other conditions which can be determined to be associated with elevated levels of hydrogen peroxide (and/or other ROS) with the aid of no more than routine experimentation.

In yet another aspect, a method of treating a disorder associated with abnormal expression or activity of dual-specificity tyrosine phosphorylation-regulated kinase 1A (DYRK1A) comprises administering to an individual in need thereof a pharmaceutical composition containing a therapeutically effective amount of isomyosmine or a pharmaceutically acceptable salt thereof.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Figure 1:
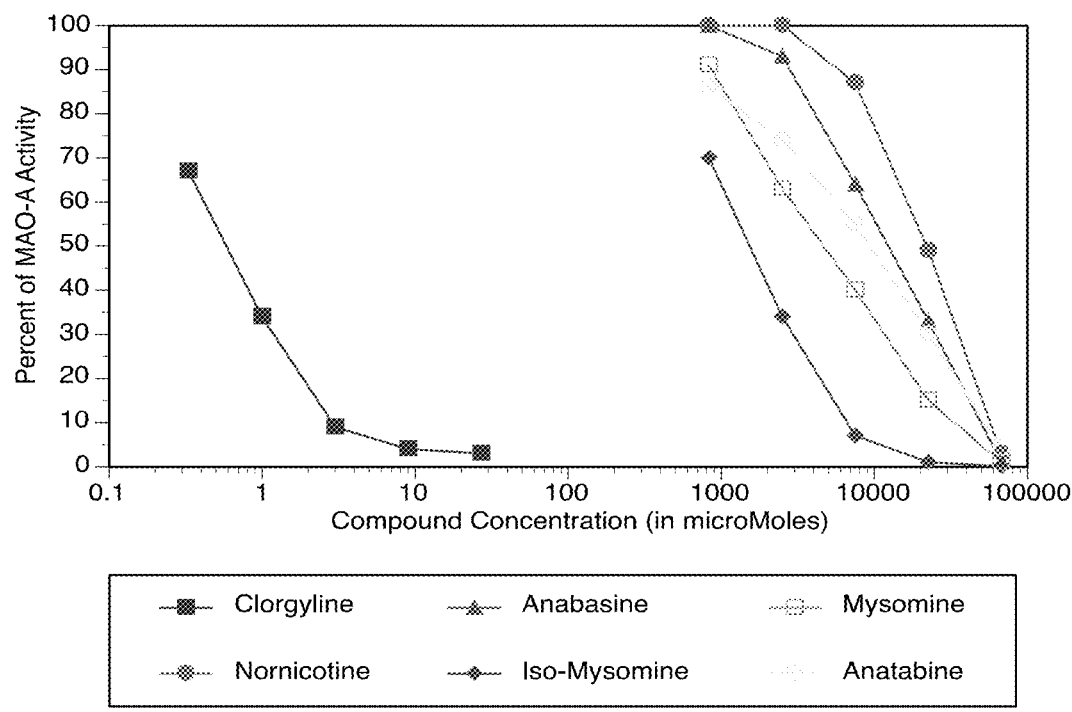
FIG. 1 is a graph showing the ability of isomyosmine, myosmine, anatabine, anabasine, and nomicotine to inhibit the enzymatic activity of MAO-A.

Aspects of the present specification disclose, in part, a pharmaceutical composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings;

antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

Isomyosmine

A pharmaceutical composition may contain isomyosmine. Isomyosmine (3-(3,4-dihydro-2H-pyrrol-2-yl)-pyridine) is a nicotine related alkaloid present in solanecea plants containing nicotine.

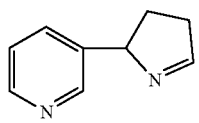 [SMILES: C1=NC(c2cccnc2)CC1]

Isomyosmine may be prepared synthetically using known techniques, and also is commercially available from several chemical suppliers. Isomyosmine has two optical isomers (+/−) owing to an asymmetric carbon atom within its pyrrole ring that joins to the pyridine ring. Unless otherwise clear from context, the term "isomyosmine," as used herein, is inclusive of enantiomeric mixtures (+/−) including racemic mixtures, as well as isolated forms of one or the other enantiomer.

Unless otherwise clear from context, "isomyosmine" as used herein refers to both salt and non-salt forms of isomyosmine. Non-limiting examples of possible salts are described in P. H. Stahl et al., Handbook of Pharmaceutical Salts: Properties, Selection and Use, Weinheim/Zürich:Wiley-VCHNHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

As an alternative to preparing isomyosmine synthetically, isomyosmine can be obtained by extraction from tobacco or other sources in which it occurs naturally. For example, a tobacco extract may be prepared from cured tobacco stems, lamina, or both. In the extraction process, cured tobacco material is extracted with a solvent, typically water, ethanol, steam, or carbon dioxide. The resulting solution contains the soluble components of the tobacco, including isomyosmine. Isomyosmine may be purified from the other components of the tobacco using suitable techniques such as liquid chromatography.

In pharmaceutical applications, an isolated form of isomyosmine generally is used. An "isolated form of isomyosmine," as used herein, refers to isomyosmine that either has been prepared synthetically or has been substantially separated from natural materials in which it occurs. The isolated form of isomyosmine should have a very high purity (including enantiomeric purity in the case where an enantiomer is used). In the case of synthetic isomyosmine, for example, purity refers to the ratio of the weight of isomyosmine to the weight of the end reaction product. In the case of isolating isomyosmine from native material, for example, purity refers to the ratio of the weight of isomyosmine to the total weight of the isomyosmine-containing extract. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

While not wanting to be bound by theory, it is believed that isomyosmine has a unique ability to affect basic cell function and directly and/or indirectly inhibit the production of Reactive Oxygen Species (ROS), particularly hydrogen peroxide ($H_2O_2$). Cells typically have mitochondria, which is prone to breaking down to form $H_2O_2$. In some aspects, isomyosmine is believed to help restore mitochondria function or, stated differently, treat mitochondria dysfunction. Isomyosmine is an inhibitor of monoamine oxidase (including MAO-A and MAO-B), an enzyme that catalyzes the production of hydrogen peroxide.

Isomyosmine is also believed to regulate dual-specificity tyrosine phosphorylation-regulated kinase 1A (DYRK1A). DYRK1A plays a role in regulating the body's immune response as well as in viral replication. Abnormal expression or activity of DYRK1A also has been associated with neuropsychiatric disorders including Down's syndrome and Alzheimer's disease. Owing to its ability to regulate DYRK1A, isomyosmine may be effective in treating a wide variety of disorders ranging from cancers to viral infections and high blood pressure.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In one embodiment, a pharmaceutical composition comprises isomyosmine and a pharmaceutically acceptable adjuvant. In another embodiment, a pharmaceutical composition disclosed herein comprises isomyosmine, a pharmaceutically acceptable solvent, and a pharmaceutically acceptable adjuvant. In aspects of this embodiment, a pharmaceutical composition disclosed herein may further comprise a pharmaceutically acceptable stabilizing agent. In other aspects of this embodiment, a pharmaceutical composition disclosed herein may further comprise a pharmaceutically acceptable carrier, a pharmaceutically acceptable component, or both pharmaceutically acceptable carrier and pharmaceutically acceptable component.

Compositions may contain isomyosmine, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity.

References herein to "therapeutic compound" may refer to isomyosmine, an active compound other than isomyosmine as described herein, or both.

In an embodiment, a therapeutic compound disclosed herein has an anti-inflammatory activity capable of reducing the levels of an inflammation-inducing molecule. In an aspect of this embodiment, a therapeutic compound disclosed herein has an anti-inflammatory activity capable of reducing the levels of substance P(SP), calcitonin gene-related peptide (CGRP), glutamate, or a combination thereof. In other aspects of this embodiment, a therapeutic compound disclosed herein has an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of SP, CGRP, glutamate, or a combination thereof released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor gamma (PPAR-γ) signaling. PPAR-γ signaling pathway 1) induces apoptosis of macrophage M1 cells, thereby reducing the levels of Th1 pro-inflammatory cytokines and 2) promotes differentiation of monocytes into macrophage M2 cells. Macrophage M2 cells produce and release Th2 anti-inflammatory cytokines.

In an embodiment, a therapeutic compound has an anti-inflammatory activity capable of reducing the levels of an inflammation inducing prostaglandin. In other aspects of this embodiment, a therapeutic compound has an anti-inflammatory activity capable of reducing the levels of an inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound has an anti-inflammatory activity capable of reducing the levels of an inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound has an anti-inflammatory activity substantially similar to 15dPGJ2. In aspects of this embodiment, a therapeutic compound has an anti-inflammatory activity that is, e.g., at least 5%, at least 15%, at least 25%, at least 50%, at least 55%, at least 60%, at least 65%, at least 70%, at least 75%, at least 80%, at least 85%, at least 90% or at least 95% of the activity observed for 15dPGJ2. In other aspects of this embodiment, a therapeutic compound has an anti-inflammatory activity that is in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50% of the activity observed for 15dPGJ2.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGJ2 (a prostaglandin), whereas PPAR-α is activated by leukotriene B4.

In some aspects, a therapeutic compound may have an anti-inflammatory activity capable of stimulating some or all PPAR signaling pathways. It is contemplated that such a therapeutic compound therefore may act as a PPAR pan-agonist or possibly as a selective PPAR agonist.

In other aspects, a therapeutic compound has an anti-inflammatory activity capable of stimulating a PPAR-α signaling pathway. In aspects of this embodiment, a therapeutic compound disclosed herein stimulates a PPAR-α signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-α signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In some aspects, a therapeutic compound has an anti-inflammatory activity capable of stimulating a PPAR-δ signaling pathway. A therapeutic compound may, for example, stimulate a PPAR-δ signaling pathway by at least 5%, at least 15%, at least 25%, at least 50%, at least 60%, at least 70%, at least 80%, or at least 90%. In some cases, a therapeutic compound stimulates a PPAR-δ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In some aspects, a therapeutic compound has an anti-inflammatory activity capable of stimulating a PPAR-γ signaling pathway. A therapeutic compound may be capable of binding to all isoforms of PPAR-γ, or may be capable of selectively binding to either PPAR-γ1, PPAR-γ2, PPAR-γ3, or any combination of two thereof. A therapeutic compound may stimulate a PPAR-γ signaling pathway by, e.g., at least 5%, at least 15%, at least 25%, at least 50%, at least 60%, at least 70%, at least 80%, or at least 90%. A therapeutic compound may stimulate a PPAR-γ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

Macrophages are activated and polarized into distinct phenotypes expressing unique cell surface molecules and secreting discrete sets of cytokines and chemokines. The classical M1 phenotype supports pro-inflammatory Th1 responses driven by cytokines such as, e.g., Interleukin-6 (IL-6), IL-12 and IL-23, while the alternate M2 phenotype is generally supportive of anti-inflammatory processes driven by IL-10. M2 cells can be further classified into subsets, M2a, M2b, and M2c, based on the type of stimulation and the subsequent expression of surface molecules and cytokines.

In yet another embodiment, a therapeutic compound has an anti-inflammatory activity capable of promoting the resolving phenotypic change of M1 to M2. A therapeutic compound may have an anti-inflammatory activity capable of inducing apoptosis of macrophage M1 cells. A therapeutic compound may have an anti-inflammatory activity capable of promoting differentiation of macrophage M2 cells. In yet another aspect of this embodiment, a therapeutic compound disclosed herein has an anti-inflammatory activity capable of inducing apoptosis of macrophage M1 cells and promoting differentiation of macrophage M2 cells.

In still another embodiment, a therapeutic compound has an anti-inflammatory activity capable of modulating Th1 and Th2 cytokines. A therapeutic compound may have an anti-inflammatory activity capable of reducing the levels of Interferon-gamma (IFN-γ), tumor necrosis factor-alpha (TNF-α), interleukin-12 (IL-12), or a combination thereof released from a Th1 cell. In other aspects of this embodiment, a therapeutic compound may have an anti-inflammatory activity capable of reducing the levels of IFN-γ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. In yet other aspects of this embodiment, a therapeutic compound may have an anti-inflammatory activity capable of reducing the levels of IFN-γ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound has an anti-inflammatory activity capable of increasing the levels of IL-10 released from a Th2 cell. A therapeutic compound may have an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound may have an anti-inflammatory activity capable of increasing the levels of IL-10 released from a Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound has an anti-inflammatory activity capable of reducing the levels of IFN-γ, TNF-α, IL-12, or a combination thereof released from a Th1 cell and increasing the levels of IL-10 released from a Th2 cell. A therapeutic compound may have an anti-inflammatory activity capable of reducing the levels of IFN-γ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound may have an anti-inflammatory activity capable of reducing the levels of IFN-γ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, and capable of increasing the levels of IL-10 released from a Th2 cell in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In addition to isomyosmine, pharmaceutical formulations as described herein may include additional therapeutic compound(s) such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

A therapeutic compound may have a log P value indicating that the compound is soluble in an organic solvent. As used herein, the term "log value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 nm$^2$, less than 7.0 nm$^2$, less than 6.0 nm$^2$, less than 5.0 nm$^2$, less than 4.0 nm$^2$, or less than 3.0 nm$^2$.

In some aspects, a therapeutic compound may be a PPAR-γ agonist. Examples of a suitable PPAR-γ agonist include, without limitation, benzbromarone, a cannabidiol, cilostazol, curcumin, delta(9)-tetrahydrocannabinol, glycyrrhetinic acid, indomethacin, irbesartan, monascin, mycophenolic acid, resveratrol, 6-shogaol, telmisartan, a thiazolidinedione like rosiglitazone, pioglitazone, and troglitazone, a NSAID, and a fibrate. Other suitable PPAR-γ agonists are described in Masson et al. US 2011/0195993 A1, the disclosure of which is hereby incorporated by reference.

A therapeutic compound may be a nuclear receptor binding agent. Examples of a suitable nuclear receptor binding agent include, without limitation, a retinoic acid receptor (RAR) binding agent, a retinoid X receptor (RXR) binding agent, a liver X receptor (LXR) binding agent and a vitamin D binding agent.

A therapeutic compound may be an anti-hyperlipidemic agent. There are several classes of anti-hyperlipidemic agents (also known as hypolipidemic agents). They may differ in both their impact on the cholesterol profile and adverse effects. For example, some may lower low density lipoprotein (LDL), while others may preferentially increase high density lipoprotein (HDL). Clinically, the choice of an agent will depend on the cholesterol profile of an individual, cardiovascular risk of an individual, and/or the liver and kidney functions of an individual. Examples of a suitable anti-hyperlipidemic agent include, without limitation, a fibrate, a statin, a tocotrienol, a niacin, a bile acid sequestrants (resin), a cholesterol absorption inhibitor, a pancreatic lipase inhibitor, and a sympathomimetic amine.

A therapeutic compound may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, bezafibrate, ciprofibrate, clofibrate, gemfibrozil, and fenofibrate.

A therapeutic compound may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, atorvastatin, fluvastatin, lovastatin, pitavastatin, pravastatin, rosuvastatin, and simvastatin.

A therapeutic compound may be a tocotrienol. Tocotrienols are another class of HMG-CoA reductase inhibitors and may be used to lower LDL and/or cholesterol levels by inducing hepatic LDL receptor up-regulation and/or decreasing plasma LDL levels. Examples of a suitable tocotrienol include, without limitation, a γ-tocotrienol and a δ-tocotrienol.

A therapeutic compound may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of very-low-density lipoproteins (VLDL) and cholesterol by the liver. By lowering VLDL levels, a niacin may also increase the level of HDL in blood. Examples of a niacin include, without limitation, acipimox, niacin, nicotinamide, and vitamin B3.

A therapeutic compound may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, cholestyramine, colesevelam, and colestipol.

In some aspects, a therapeutic compound may be a cholesterol absorption inhibitor. Cholesterol absorption inhibitors are a class of therapeutic compounds that inhibits the absorption of cholesterol from the intestine. Decreased cholesterol absorption leads to an up-regulation of LDL-receptors on the surface of cells and an increased LDL-cholesterol uptake into these cells, thus decreasing levels of LDL in the blood plasma. Examples of a suitable cholesterol absorption inhibitor include, without limitation, ezetimibe, a phytosterol, a sterol and a stanol.

A therapeutic compound may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, orlistat.

A therapeutic compound may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, clenbuterol, salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine.

In another aspect, isomyosmine may be administered for treating tobacco or other substance addiction, including promoting smoking cessation or otherwise assisting individuals in reducing or eliminating cravings for nicotine or dependence on nicotine. Isomyosmine was found to be a potent inhibitor of monoamine oxidase (MAO), including both MAO-A and MAO-B. Through these and/or other mechanisms, including one or more of the aforementioned anti-inflammatory mechanisms, pharmaceutical compositions containing isomyosmine may be particularly effective for treating tobacco addiction and/or for assisting individuals in reducing or eliminating cravings for nicotine or dependence on nicotine. For some individuals, the administration of isomyosmine may be effective for treating more than one disorder. For example, COPD is a relatively common disorder among smokers. Compositions containing isomyosmine may be useful for assisting such individuals not only with smoking cessation, but also in the treatment of COPD and/or other chronic inflammation-related disorders suffered by the individual, whether or not caused by or related to smoking.

A therapeutic compound disclosed herein may be an ester of a therapeutic compound. In general, an ester of a therapeutic compound increases the log P value relative to the same therapeutic compound without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

In another embodiment, a pharmaceutical composition does not comprise a pharmaceutically acceptable solvent as previously described. In an aspect of this embodiment, a pharmaceutical composition may comprise a therapeutic compound and a pharmaceutically acceptable adjuvant but without a pharmaceutically acceptable solvent.

A pharmaceutical composition may comprise a therapeutic compound in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically acceptable alcohol. As used herein, the term "alcohol" refers to an organic molecule comprising a hydroxyl functional group (—OH) bonded to a carbon atom, where the carbon atom is saturated. In aspects of this embodiment, the alcohol may be, e.g., a $C_{1-4}$ alcohol, a $C_{2-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexyl and 2-(2-propyl)-5-methyl-cyclohexane-1-ol.

In another embodiment, a solvent may comprise an ester of pharmaceutically acceptable alcohol and an acid. Suitable pharmaceutically acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically acceptable solid solvent includes, without limitation, menthol and PEG polymers described above.

Aspects of the present specification disclose, in part, a pharmaceutically acceptable adjuvant. An adjuvant is a pharmacological agent that modifies the effect of other agents, such as one or more therapeutic compounds disclosed herein. In addition, an adjuvant disclosed herein may be used as a solvent that dissolves a therapeutic compound disclosed herein, forming an adjuvant solution. An adjuvant may facilitate delivery of a therapeutic compound in a manner that more effectively inhibits a pro-inflammatory response. In one embodiment, an adjuvant facilitates the delivery of a therapeutic compound into macrophages.

A pharmaceutical composition may comprise a pharmaceutically acceptable adjuvant in an amount sufficient to mix with a solution or an emulsion. In other aspects of this embodiment, a pharmaceutical composition may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride, or a mixture thereof.

A lipid useful in the pharmaceutical compositions may be a pharmaceutically acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, capryllic acid (8:0), pelargonic acid (9:0), capric acid (10:0), undecylic acid (11:0), lauric acid (12:0), tridecylic acid (13:0), myristic acid (14:0), myristoleic acid (14:1), pentadecyclic acid (15:0), palmitic acid (16:0), palmitoleic acid (16:1), sapienic acid (16:1), margaric acid (17:0), stearic acid (18:0), oleic acid (18:1), elaidic acid (18:1), vaccenic acid (18:1), linoleic acid (18:2), linoelaidic acid (18:2), α-linolenic acid (18:3), γ-linolenic acid (18:3), stearidonic acid (18:4), nonadecylic acid (19:0), arachidic acid (20:0), eicosenoic acid (20:1), dihomo-γ-linolenic acid (20:3), mead acid (20:3), arachidonic acid (20:4), eicosapentaenoic acid (20:5), heneicosylic acid (21:0), behenic acid (22:0), erucic acid (22:1), docosahexaenoic acid (22:6), tricosylic acid (23:0), lignoceric acid (24:0), nervonic acid (24:1), pentacosylic acid (25:0), cerotic acid (26:0), heptacosylic acid (27:0), montanic acid (28:0), nonacosylic acid (29:0), melissic acid (30:0), henatriacontylic acid (31:0), lacceroic acid (32:0), psyllic acid (33:0), geddic acid (34:0), ceroplastic acid (35:0), and hexatriacontylic acid (36:0).

In an embodiment, an adjuvant may be a pharmaceutically acceptable saturated or unsaturated fatty acid. A saturated or unsaturated fatty acid may comprise, e.g., at least 8, at least 10, at least 12, at least 14, at least 16, at least 18, at least 20, at least 22, at least 24, at least 26, at least 28, or at least 30 carbon atoms. In some instances, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

A pharmaceutically acceptable saturated or unsaturated fatty acid may be liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20°

C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., or about −15° C. to about 0° C.

In another embodiment, an adjuvant may comprise one kind of pharmaceutically acceptable fatty acid. An adjuvant may comprise, for example, only palmitic acid, only stearic acid, only oleic acid, only linoleic acid, or only linolenic acid. Alternatively, an adjuvant may comprise a plurality of different pharmaceutically acceptable fatty acids. An adjuvant may comprise, e.g., two or more different fatty acids, three or more different fatty acids, four or more different fatty acids, five or more different fatty acids, or six or more different fatty acids.

In other aspects of this embodiment, an adjuvant may comprise two or more different pharmaceutically acceptable fatty acids including at least palmitic acid, stearic acid, oleic acid, linoleic acid and/or linolenic acid, and any combination thereof. An adjuvant may comprise a ratio of palmitic acid and/or stearic acid and/or oleic acid:linoleic acid and/or linolenic acid of, e.g., at least 2:1, at least 3:1, at least 4:1, at least 5:1, at least 6:1, at least 7:1, at least 8:1, at least 9:1, at least 10:1, at least 15:1, or at least 20:1. In some examples, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

In other aspects of this embodiment, an adjuvant may comprise four or more different pharmaceutically acceptable fatty acids including at least palmitic acid, stearic acid, oleic acid, linoleic acid and/or linolenic acid, and any combination thereof. In other aspects of this embodiment, an adjuvant may comprise a ratio of palmitic acid:stearic acid: linolenic acid:linoleic acid of, e.g., 10:10:1:1, 9:9:1:1, 8:8: 1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid:stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions may be a pharmaceutically acceptable omega fatty acid. Non-limiting examples of an omega fatty acid include omega-3, omega-6, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, hexadecatrienoic acid (16:3), α-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), clupanodonic acid (22:5), docosahexaenoic acid (22: 6), tetracosapentaenoic acid (24:5), and tetracosahexaenoic acid (nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, linoleic acid (18:2), gamma-linolenic acid (18:3), calendic acid (18:3), eicosadienoic acid (20:2), dihomo-gamma-linolenic acid (20:3), arachidonic acid (20: 4), docosadienoic acid (22:2), adrenic acid (22:4), docosapentaenoic acid (22:5), tetracosatetraenoic acid (24:4), and tetracosapentaenoic acid (24:5). Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, oleic acid (18:1), elaidic acid (18:1), eicosenoic acid (20:1), mead acid (20:3), erucic acid (22:1), and nervonic acid (24:1).

A lipid useful in the pharmaceutical compositions disclosed herein may be a pharmaceutically acceptable oil. An oil includes any fatty acid that is liquid at normal room temperature, such as, e.g. about 20° C. In contrast, a fat includes any fatty acid that is solid at normal room temperature, such as, e.g. about 20° C. An oil suitable as a lipid useful in the pharmaceutical compositions disclosed herein, may be a natural oil or a vegetable oil. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, walnut oil, wheat germ oil, or a mixture thereof. Each of these oils is commercially available from a number of sources well recognized by those skilled in the art.

An oil is typically a mixture of various fatty acids. For example, rapeseed oil, obtained from the seeds of Brassica napus, includes both omega-6 and omega-3 fatty acids in a ratio of about 2:1. As another example, linseed oil, obtained from the seeds of Linum usitatissimum, includes about 7% palmitic acid, about 3.4-4.6% stearic acid, about 18.5-22.6% oleic acid, about 14.2-17% linoleic acid, and about 51.9-55.2% α-linolenic acid. In some instances, a pharmaceutical composition comprises an oil including at least two different fatty acids, at least three different fatty acids, at least four different fatty acids, at least five different fatty acids, or at least six different fatty acids.

A lipid useful in the pharmaceutical compositions may be a pharmaceutically acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

In some instances, compositions may include one or more pharmaceutically acceptable stabilizing agents. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically acceptable stabilizing agent may comprise a pharmaceutically acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

In an aspect of this embodiment, an emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), such as Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, such as BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-cholamidopropyl)dimethylammonio]-1-propanesulfonate (CHAPS); 3-[(3-cholamidopropyl)dimethylammonio]-2-hydroxy-1-prop anesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

In an aspect of this embodiment, an emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (NEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

In an aspect of this embodiment, an emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, Maackia anurensis leukoagglutinin, Maackia anurensis hemoagglutinin, Ulex europaeus agglutinin, and Aleuria aurantia lectin.

In an aspect of this embodiment, an emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline; one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

In one embodiment, a pharmaceutically acceptable stabilizing agent does not comprise a pharmaceutically acceptable emulsifying agent.

In another embodiment, a pharmaceutical composition does not comprise a pharmaceutically acceptable emulsifying agent.

The pharmaceutical compositions may act as a delivery system that enables the therapeutic compound(s) to be more effectively delivered or targeted to a cell type, tissue, organ, or region of the body in a manner that more effectively inhibits a pro-inflammatory response. This inhibition results in an improved treatment of a chronic inflammation. For example, a pharmaceutical composition may facilitate the delivery of a therapeutic compound disclosed herein into macrophages. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body. Chylomicrons are one of the five major groups of lipoproteins, the others being VLDL, IDL, low-density lipoproteins (LDL), high-density lipoproteins (HDL), that enable fats and cholesterol to move within the water-based solution of the bloodstream.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration of the pharmaceutical compositions disclosed herein are processed into micelles while in the gastrointestinal tract, absorbed by enterocytes and assembled into nascent chylomicrons, remain associated with chylomicron remnants taken up by the liver, and ultimately loaded into macrophages.

Aspects of the present specification disclose, in part, a method of preparing a pharmaceutical composition disclosed herein. A method disclosed herein comprises the step of contacting a pharmaceutically acceptable adjuvant disclosed herein with a therapeutic compound disclosed herein under conditions which allow the therapeutic compound to dissolve in the pharmaceutically acceptable adjuvant, thereby forming a pharmaceutical composition disclosed herein.

Other aspects of the present specification include a method of preparing a pharmaceutical composition. A method may comprise the steps of a) contacting a pharmaceutically acceptable solvent with a therapeutic compound under conditions which allow the therapeutic compound to dissolve in the pharmaceutically acceptable solvent, thereby forming a solution; and b) contacting the solution formed in step (a) with a pharmaceutically acceptable adjuvant disclosed herein under conditions which allow the formation of a pharmaceutical composition. The methods of preparing may further comprise a step (c) of removing the pharmaceutically acceptable solvent from the pharmaceutical composition.

The amount of therapeutic compound that is contacted with the pharmaceutically acceptable solvent in step (a) of the method may vary widely. Factors that may influence the amount of a therapeutic compound used include, among others, the final amount the therapeutic compound desired in the pharmaceutical composition, the desired concentration of a therapeutic compound in the solution, the hydrophobicity of the therapeutic compound, the lipophobicity of the therapeutic compound, the temperature under which the contacting step (a) is performed, and the time under which the contacting step (a) is performed.

The volume of a pharmaceutically acceptable solvent used in step (a) of the method also may vary over a wide range. Factors that may influence the volume of pharmaceutically acceptable solvent used include, among others, the final amount of pharmaceutical composition desired, the desired concentration of a therapeutic compound in the solution, the hydrophobicity of the therapeutic compound, and the lipophobicity of the therapeutic compound.

In aspects of this embodiment, the amount of a therapeutic compound that is contacted with the solvent in step (a) may be, e.g., at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In other aspects of this embodiment, the amount of a therapeutic compound that is contacted with the solvent in step (a) may be in the range of, e.g., about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In other aspects of this embodiment, the amount of a therapeutic compound that is dissolved in the solvent in step (a) may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, or about 200 mg to about 1,500 mg.

Step (a) may be carried out at room temperature, in order to allow a therapeutic compound to dissolve fully in the pharmaceutically acceptable solvent. However, in other embodiments of the method, step (a) may be carried out at a temperature that is greater than room temperature, e.g., greater than 21° C., greater than 25° C., greater than 30° C., greater than 35° C. or greater than 3TC. In certain cases, Step (a) may be carried out at temperatures below room temperature, in order to allow a therapeutic compound to dissolve fully in solvent. However, in other embodiments of the method, step (a) may be carried out at a temperature that is less than room temperature, e.g., less than 10° C., greater than 5° C., greater than 0° C., greater than −10° C. or greater than −20° C. The contacting in Step (a) may comprise mixing the therapeutic compound and the pharmaceutically acceptable solvent, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the solvent.

The concentration of a therapeutic compound in a solution may vary over a wide range. By way of example, the concentration of the therapeutic compound may be at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. The concentration of the therapeutic compound may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In some instances, the concentration of a therapeutic compound may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

The volume of a pharmaceutically acceptable adjuvant used in step (b) of the method may be any volume desired. Factors used to determine the volume of a pharmaceutically acceptable adjuvant used include, without limitation, the final amount of a pharmaceutical composition desired, the desired concentration of a therapeutic compound in the pharmaceutical composition, the ratio of solvent:adjuvant used, and the miscibility of solvent and adjuvant.

In aspects of this embodiment, the ratio of solution: adjuvant may be, e.g., at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of solution:adjuvant may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 2:1 to about 1:15, about 0:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

Step (b) may be carried out at room temperature, in order to allow the solution comprising the therapeutic compound to form the pharmaceutical composition. However, in other embodiments of the method, step (b) may be carried out at a temperature that is greater than room temperature, e.g., greater than 21° C., greater than 25° C., greater than 30° C., greater than 35° C. or greater than 37° C. In certain cases, step (b) may be carried out at temperatures below room temperature, in order to allow a therapeutic compound to dissolve fully in a pharmaceutically acceptable solvent. However, in other embodiments of the method, step (b) may be carried out at a temperature that is less than room temperature, e.g., less than 10° C., greater than 5° C., greater than 0° C., greater than −10° C. or greater than −20° C. The contacting in step (b) may comprise mixing the solution and the pharmaceutically acceptable adjuvant, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the pharmaceutical composition is formed.

In step (c), the solvent removal from a pharmaceutical composition may be accomplished using one of a variety of procedures known in the art, including, without limitation, evaporation, dialyzation, distillation, lypholization, and filtration. These removal procedures may be done under conditions of ambient atmosphere, under low pressure, or under a vacuum.

In one embodiment, step (c) may result in the complete removal of a pharmaceutically acceptable solvent from the pharmaceutical composition disclosed herein. In aspects of this embodiment, step (c) may result in, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 93%, at least 95%, at least 97%, or at least 99% removal of a pharmaceutically acceptable solvent from the pharmaceutical composition disclosed herein.

Step (c) is conducted at a temperature that allows for the evaporation of a pharmaceutically acceptable solvent disclosed herein, and as such, an evaporation temperature is solvent-dependent. Factors which influence an evaporation temperature of a solvent disclosed herein include, without limitation, the particular solvent used, the amount of solvent present, the particular therapeutic compound present, the particular adjuvant present, the stability of the therapeutic compound present, the reactivity of the therapeutic compound present, the particular atmospheric pressure used, the time desired for complete evaporation. Generally, a pharmaceutical composition will require heating if the evaporation step is conducted at ambient pressure, e.g., 1 atm. However, under high vacuum conditions, the evaporation step may be conducted at temperatures below ambient temperature, e.g., less than 22° C.

In one embodiment, removal of solvent from the pharmaceutical composition disclosed herein may be carried out at ambient atmospheric pressure and at a temperature above ambient temperature. In aspects of this embodiment, removal of solvent from the pharmaceutical composition may be carried out at ambient atmospheric pressure and at a temperature of, e.g., more than 25° C., more than 30° C., more than 35° C., more than 40° C., more than 45° C., more than 50° C., more than 55° C., more than 60° C., more than 65° C., more than 70° C., more than 80° C., or more than 85° C. In other aspects of this embodiment, removal of solvent from the pharmaceutical composition may be carried out at ambient atmospheric pressure and at a temperature in a range of, e.g., about 25° C. to about 100° C., about 25° C.

to about 95° C., about 25° C. to about 90° C., about 25° C. to about 85° C., about 25° C. to about 80° C., about 25° C. to about 75° C., about 25° C. to about 70° C., about 25° C. to about 65° C., or about 25° C. to about 60° C.

In another embodiment, removal of solvent from the pharmaceutical composition may be carried out under vacuum and at a temperature below ambient temperature. In aspects of this embodiment, removal of solvent from the pharmaceutical composition may be carried out under vacuum and at a temperature of, e.g., less than 20° C., less than 18° C., less than 16° C., less than 14° C., less than 12° C., less than 10° C., less than 8° C., less than 6° C., less than 4° C., less than 2° C., or less than 0° C. In other aspects of this embodiment, removal of solvent from the pharmaceutical composition may be carried out under vacuum and at a temperature in a range of, e.g., about −20° C. to about 20° C., about −20° C. to about 18° C., about −20° C. to about 16° C., about −20° C. to about 14° C., about −20° C. to about 12° C., about −20° C. to about 10° C., about −20° C. to about 8° C., about −20° C. to about 6° C., about −20° C. to about 4° C., about −20° C. to about 2° C., about −20° C. to about 0° C., about −15° C. to about 20° C., about −10° C. to about 20° C., about −5° C. to about 20° C., about 0° C. to about 20° C., about −10° C. to about 20° C., about −10° C. to about 18° C., about −10° C. to about 16° C., about −10° C. to about 14° C., about −10° C. to about 12° C., about −10° C. to about 10° C., about −10° C. to about 8° C., about −10° C. to about 6° C., about −10° C. to about 4° C., about −10° C. to about 2° C., or about −10° C. to about 0° C.

The final concentration of a therapeutic compound in a pharmaceutical composition disclosed herein may vary over a wide range and generally may be characterized as a therapeutically effective amount. In some aspects, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be a liquid formulation or a solid or semi-solid formulation. A liquid formulation can be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher.

A solid or semi-solid formulation may take advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature ($T_m$) of about −11° C., linoleic acid has a $T_m$ of about −5° C., oleic acid has a $T_m$ of about 16° C., palmitic acid has a $T_m$ of about 61-62° C., and Stearic acid has a $T_m$ of about 67-72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

Aspects of the present specification disclose a method of treating an individual with a chronic inflammation. In one embodiment, the method comprises the step of administering to an individual in need thereof a pharmaceutical composition as described herein, wherein administration reduces a symptom associated with the chronic inflammation, thereby treating the individual.

Aspects of the present specification disclose, in part, treating an individual suffering from a chronic inflammation. As used herein, the term "treating," refers to reducing or eliminating in an individual a clinical symptom of a chronic inflammation; or delaying or preventing in an individual the onset of a clinical symptom of a chronic inflammation. For example, the term "treating" can mean reducing a symptom of a condition characterized by a chronic inflammation by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with chronic inflammation are well known and can be determined by a person of ordinary skill in the art by taking into account factors, including, without limitation, the location of the chronic inflammation, the cause of the chronic inflammation, the severity of the chronic inflammation, and/or the tissue or organ affected by the chronic inflammation. Those of skill in the art will know the appropriate symptoms or indicators associated with a specific type of chronic inflammation and will know how to determine if an individual is a candidate for treatment as disclosed herein.

Chronic inflammation symptoms include, without limitation, edema, hyperemia, erythema, bruising, tenderness, stiffness, aches, swollenness, fever, chills, stuffy nose, stuffy head, breathing problems, fluid retention, blood clots, loss of appetite, increased heart rate, formation of granulomas, fibrinous, pus, non-viscous serous fluid, or ulcer and pain. The actual symptoms associated with a chronic inflammation are well known and can be determined by a person of ordinary skill in the art by taking into account factors, including, without limitation, the location of the inflammation, the cause of the inflammation, the severity of the inflammation, the tissue or organ affected, and the associated disorder.

Specific patterns of chronic inflammation are seen during particular situations that arise in the body, such as when inflammation occurs on an epithelial surface, or pyogenic bacteria are involved. For example, granulomatous inflammation is an inflammation resulting from the formation of granulomas arising from a limited but diverse number of diseases, include, without limitation, tuberculosis, leprosy, sarcoidosis, and syphilis. Purulent inflammation is an inflammation resulting in large amount of pus, which consists of neutrophils, dead cells, and fluid. Infection by pyogenic bacteria such as staphylococci is characteristic of this kind of inflammation. Serous inflammation is an inflammation resulting from copious effusion of non-viscous serous fluid, commonly produced by mesothelial cells of serous membranes, but may be derived from blood plasma. Skin blisters exemplify this pattern of inflammation. Ulcerative inflammation is an inflammation resulting from the necrotic loss of tissue from the epithelial surface, exposing lower layers and forming an ulcer.

A chronic inflammation symptom can be associated with a large, unrelated group of disorders which underlay a variety of diseases and disorders. The immune system is often involved with chronic inflammatory disorders, demonstrated in both allergic reactions and some myopathies, with many immune system disorders resulting in abnormal inflammation. Non-immune diseases with etiological origins in chronic inflammatory processes include cancer, atherosclerosis, and ischaemic heart disease. Non-limiting examples of disorders exhibiting chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, Crone's disease, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis.

In one embodiment, a chronic inflammation comprises a tissue inflammation. Tissue inflammation is a chronic inflammation that is confined to a particular tissue or organ. In aspect of this embodiment, a tissue inflammation comprises, e.g., a skin inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

In another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In another embodiment, a chronic inflammation comprises an autoimmune disorder. Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjogren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, amyotrophic lateral sclerosis, anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD), diabetes mellitus type 1 (IDDM), endometriosis, fibromyalgia, Goodpasture's syndrome, Graves' disease, Guillain-Barre syndrome (GBS), Hashimoto's thyroiditis, hidradenitis suppurativa, idiopathic thrombocytopenic purpura, inflammatory bowel disease, interstitial cystitis, lupus (including discoid lupus erythematosus, drug-induced lupus erythematosus, lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjogren's syndrome, tenosynovitis, vasculitis, and vitiligo.

In another embodiment, a chronic inflammation comprises a myopathy. Myopathies are caused when the immune system inappropriately attacks components of the muscle, leading to inflammation in the muscle. A myopathy includes an inflammatory myopathy and an auto-immune myopathy. Myopathies include, without limitation, dermatomyositis, inclusion body myositis, and polymyositis.

In another embodiment, a chronic inflammation comprises a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

In another embodiment, a chronic inflammation comprises a skin disorder. Skin disorders include, without limitation, an acne, including acne vulgaris, a bullous phemigoid, a dermatitis, including atopic dermatitis and chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, lichen planus, psoriasis including plaqure psoriasis, nail psoriasis, guttate psoriasis, scalp psoriasis, inverse psoriasis, pustular psoriasis, erythrodermis psoriasis, and psoriatic arthritis, rosacea and scleroderma including morphea.

In another embodiment, a chronic inflammation comprises a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

In another embodiment, a chronic inflammation comprises a cardiovascular disease. When LDL cholesterol becomes embedded in arterial walls, it can invoke an immune response. Chronic inflammation eventually can damage the arteries, which can cause them to burst. Cardiovascular disease is any of a number of specific diseases that affect the heart itself and/or the blood vessel system, especially the veins and arteries leading to and from the heart. There are more than 60 types of cardiovascular disorders including, without limitation, a hypertension, endocarditis, myocarditis, heart valve dysfunction, congestive heart failure, myocardial infarction, a diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombphlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night.

In some aspects, a chronic inflammation comprises a cancer. Inflammation orchestrates the microenvironment around tumors, contributing to proliferation, survival and migration. For example, fibrinous inflammation results from a large increase in vascular permeability which allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. In another example, a cancer is an inflammatory cancer like a NF-κB-driven inflammatory cancer.

In some instances, drugs which otherwise may be effective for treating cancers become ineffective or less effective due to the environment ("microenvironment") created around tumors. These microenvironments normally are associated with high levels of Reactive Oxygen Species (ROS), notably hydrogen peroxide. Fibroblasts also produce hydrogen peroxide. Oxidation also is prone to occur outside of cancer cells.

In one aspect, a therapeutic compound modifies a tumor microenvironment, such as by reducing the concentration of hydrogen peroxide and/or other ROS. By modifying the microenvironment in which a cancer thrives, the therapeutic compound may help restore normal function of endogenous species. Further, modification of the microenvironment may improve the efficacy other cancer therapies, including chemotherapies. To the extent that the presence of hydrogen peroxide and/or other ROS may be responsible for oncogenesis, the therapeutic compound further may function to prevent or delay the onset of a tumor. See, e.g., Poehlmann et al., "Repeated $H_2O_2$ exposure drives cell cycle progression in an in vitro model of ulcerative colitis," J Cell Mol. Med. 2013 December; 17(12): 1619-1631.

In another embodiment, a chronic inflammation comprises a pharmacologically-induced inflammation. Certain drugs or exogenic chemical compounds are known to affect inflammation. For example, Vitamin A deficiency causes an increase in an inflammatory response. Certain illicit drugs such as cocaine and ecstasy may exert some of their detrimental effects by activating transcription factors intimately involved with inflammation (e.g., NF-κB).

In another embodiment, a chronic inflammation comprises an infection. An infectious organism can escape the confines of the immediate tissue via the circulatory system or lymphatic system, where it may spread to other parts of the body. If an organism is not contained by the actions of acute inflammation it may gain access to the lymphatic system via nearby lymph vessels. An infection of the lymph vessels is known as lymphangitis, and infection of a lymph node is known as lymphadenitis. A pathogen can gain access to the bloodstream through lymphatic drainage into the circulatory system. Infections include, without limitation, bacterial cystitis, bacterial encephalitis, pandemic influenza, viral encephalitis, and viral hepatitis (A, B and C).

In another embodiment, a chronic inflammation comprises a tissue or organ injury. Tissue or organ injuries include, without limitation, a burn, a laceration, a wound, a puncture, or a trauma.

In another embodiment, a chronic inflammation comprises a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. A transplant rejection can be classified as a hyperacute rejection, an acute rejection, or a chronic rejection. Chronic rejection of a transplanted organ or tissue is where the rejection is due to a poorly understood chronic inflammatory and immune response against the transplanted tissue. Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. Acute and chronic GVHD appear to involve different immune cell subsets, different cytokine profiles, somewhat different host targets, and respond differently to treatment.

In another embodiment, a chronic inflammation comprises a Th1-mediated inflammatory disease. In a well-functioning immune system, an immune response should result in a well-balanced pro-inflammatory Th1 response and anti-inflammatory Th2 response that is suited to address the immune challenge. Generally speaking, once a pro-inflammatory Th1 response is initiated, the body relies on the anti-inflammatory response invoked by a Th2 response to counteract this Th1 response. This counteractive response includes the release of Th2 type cytokines such as, e.g., IL-4, IL-5, and IL-13 which are associated with the promotion of IgE and eosinophilic responses in atopy, and also IL-10, which has an anti-inflammatory response. A Th1-mediated inflammatory disease involves an excessive pro-inflammatory response produced by Th1 cells that leads to chronic inflammation. The Th1-mediated disease may be virally, bacterially or chemically (e.g., environmentally) induced. For example, a virus causing the Th1-mediated disease may cause a chronic or acute infection, which may cause a respiratory disorder or influenza.

In another embodiment, a chronic inflammation comprises a chronic neurogenic inflammation. Chronic neurogenic inflammation refers to an inflammatory response initiated and/or maintained through the release of inflammatory molecules like SP or CGRP which released from peripheral sensory nerve terminals (i.e., an efferent function, in contrast to the normal afferent signaling to the spinal cord in these nerves). Chronic neurogenic inflammation includes both primary inflammation and secondary neurogenic inflammation. As used herein, the term "primary neurogenic inflammation" refers to tissue inflammation (inflammatory symptoms) that is initiated by, or results from, the release of substances from primary sensory nerve terminals (such as C and A-delta fibers). As used herein, the term "secondary neurogenic inflammation" refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. The net effect of both forms (primary and secondary) of chronic neurogenic inflammation is to have an inflammatory state that is maintained by the sensitization of the peripheral sensory nerve fibers. The physiological consequence of the resulting chronic neurogenic inflammation depends on the tissue in question, producing, such as, e.g., cutaneous pain (allodynia, hyperalgesia), joint pain and/or arthritis, visceral pain and dysfunction, pulmonary dysfunction, asthma, chronic obstructive pulmonary disease (COPD), and bladder dysfunction (e.g., pain, overactive bladder).

In some aspects, a pharmaceutical composition containing isomyosmine is administered to an individual to treat a viral infection. In one example, the virus is human immunodeficiency virus (HIV). In another example, the virus is herpes simplex virus (HSV). In yet another example, the virus is human papillomavirus (HPV). Low-risk mucosal HPVs such as HPV-6 and HPV-11 cause genital warts (condyloma accuminata), whereas the high-risk HPVs cause squamous intraepithelial lesions that can progress to invasive squamous cell carcinoma. The vast majority of human cervical cancers are associated with high-risk HPV infections. HPV-16 is by far the most prevalent mucosal high-risk HPV type, followed by HPV-18 and HPV-31. Approximately 20% of oral cancers, particularly oropharyngeal carcinomas in patients that lack the classical risk factors of tobacco and alcohol abuse, are also high-risk HPV positive. Other anogenital tract malignancies that are also frequently associated with high-risk HPV infections include penile and vulvovaginal cancers as well as anal carcinomas, which frequently occur in individuals with human immunodeficiency virus (HIV)-associated AIDS.

In one aspect, isomyosmine may be administered to individual to treat high blood pressure (hypertension). Isomyosmine is believed to treat symptoms of high blood pressure and hypertension by restoring normal function to cells in the bloodline.

A composition or compound as described herein may be administered to an individual. An individual is typically a human being. Typically, any individual who is a candidate for a conventional chronic inflammation treatment is a candidate for a chronic inflammation treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount," "effective dose," or "therapeutically effective dose," and when used in reference to treating a chronic inflammation refers to the minimum dose of a therapeutic compound disclosed herein necessary to achieve the desired therapeutic effect and includes a dose sufficient to reduce a symptom associated with a chronic inflammation. The effectiveness of a therapeutic compound disclosed herein in treating a chronic inflammation can be determined by observing an improvement in an individual based upon one or more clinical symptoms, and/or physiological indicators associated with the condition. An improvement in a chronic inflammation also can be indicated by a reduced need for a concurrent therapy.

The appropriate effective amount of a therapeutic compound disclosed herein to be administered to an individual for a particular chronic inflammation can be determined by a person of ordinary skill in the art by taking into account factors, including, without limitation, the type of chronic inflammation, the location of the chronic inflammation, the cause of the chronic inflammation, the severity of the chronic inflammation, the degree of relief desired, the duration of relief desired, the particular therapeutic compound used, the rate of excretion of the therapeutic compound used, the pharmacodynamics of the therapeutic compound used, the nature of the other compounds to be included in the composition, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

In aspects of this embodiment, a therapeutically effective amount of a therapeutic compound disclosed herein reduces a symptom associated with a chronic inflammation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a chronic inflammation by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a chronic inflammation by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a chronic inflammation may comprise a one-time administration of an effective dose of a pharmaceutical composition disclosed herein. Alternatively, treatment of a chronic inflammation may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, upon administration to an individual, a pharmaceutical composition comprising a therapeutic compound disclosed herein results in a bio-distribution of the therapeutic compound different than a bio-distribution of the therapeutic compound included in the same pharmaceutical composition, except without an adjuvant disclosed herein.

In another embodiment, upon administration to an individual, a therapeutic compound of the pharmaceutical composition disclosed herein is delivered to a macrophage. Macrophages are one of the key cell types believed to be involved in the control of the inflammation response. The resultant high level of a therapeutic compound having anti-inflammatory activity present in the macrophages results in a clinically effective treatment of chronic inflammation. In an aspect of this embodiment, upon administration to an individual, a therapeutically effective amount of a therapeutic compound of the pharmaceutical composition disclosed herein is preferentially delivered to a macrophage. In other aspect of this embodiment, upon administration to an individual, a therapeutic compound of the pharmaceutical composition disclosed herein is substantially delivered to a macrophage. In yet other aspect of this embodiment, upon administration to an individual, the amount of a therapeutic compound of the pharmaceutical composition disclosed herein delivered to a macrophage is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a macrophage is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a pharmaceutical composition disclosed herein reduces gastric irritation. In an aspect of this embodiment, a pharmaceutical composition disclosed herein substantially reduces gastric irritation. In yet another embodiment, upon administration to an individual, a pharmaceutical composition disclosed herein reduces gastric irritation when compared to the same pharmaceutical composition disclosed herein, except without the pharmaceutically acceptable adjuvant. In an aspect of this embodiment, a pharmaceutical composition disclosed herein substantially reduces gastric irritation when compared to the same pharmaceutical composition disclosed herein, except without the pharmaceutically acceptable adjuvant. In other aspects of this embodiment, a pharmaceutical composition disclosed herein reduces gastric irritation by, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In yet other aspects of this embodiment, a pharmaceutical composition disclosed herein reduces gastric irritation in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70%.

In another embodiment, upon administration to an individual, a pharmaceutical composition reduces intestinal irritation. In an aspect of this embodiment, a pharmaceutical composition substantially reduces intestinal irritation. In yet another embodiment, upon administration to an individual, a pharmaceutical composition disclosed herein reduces intestinal irritation when compared to the same pharmaceutical composition disclosed herein, except without the pharmaceutically acceptable adjuvant. In an aspect of this embodiment, a pharmaceutical composition disclosed herein substantially reduces intestinal irritation when compared to the same pharmaceutical composition disclosed herein, except without the pharmaceutically acceptable adjuvant. In other aspects of this embodiment, a pharmaceutical composition disclosed herein reduces intestinal irritation by, e.g., at least 5%, at least 10%, at least 20%, at least 30%, at least 40%, at least 50%, at least 60%, at least 70%, at least 80%, at least 90%, or at least 100% when compared to the same pharmaceutical composition disclosed herein, except without the pharmaceutically acceptable adjuvant. In yet other aspects of this embodiment, a pharmaceutical composition disclosed herein reduces intestinal irritation by, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% when compared to the same pharmaceutical composition disclosed herein, except without the pharmaceutically acceptable adjuvant.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

The following examples illustrate but do not limit the scope of the disclosure set forth above.

Example 1

This example describes experiments for determining monoamine oxidase (MAO) inhibition for isomyosmine and other alkaloids. MAOs are enzymes located on the outer membrane of mitochondria and are involved in the catabolism of monoamine neurotransmitters. There are two well-characterized isoenzymes: MAO-A, which predominantly catabolizes serotonin and norepinephrine, and MAO-B, which preferentially catabolizes benzylamine and phenylethylamine. Dopamine and tyramine are metabolized by both isoforms.

To detect the activity of MAO, a luminescent method (MAO-Glo Assay kit, from Promega, Cat # V1401) was used. In this method, a MAO substrate (a derivative of beetle luciferin provided in the kit) is mixed with the compound to be tested (in this case, myosmine and control compounds). Then, the MAO enzymes (either A or B, purchased separately) are added to the mixture and incubated with the reaction for 1 hour at room temperature. The MAO enzymes, if not inhibited by the test compound, will convert the substrate into methyl ester luciferin. Finally, a luciferin detection reagent (provided by the kit) is added (20 minutes at room temperature) to stop the MAO reaction and convert methyl ester luciferin into D-luciferin. D-luciferin reacts with luciferase to produce a luminescent signal, which is directly proportional to the D-luciferin concentration and thus the MAO activity: the greater the amount of light produced the higher the activity of MAO. The luminescent signal is measured and recorded using a luminometer.

The following materials were obtained from Toronto Research Chemicals, North York, ON: isomyosmine, catalog # I821350; myosmine, catalog # M835000; anabasine, catalog # A637175; and nornicotine, catalog # N756995. Anatabine was obtained from Emerson Resources, Norristown, Pa.

As positive controls for the experiment, clorgyline (a well-characterized potent inhibitor of MAO-A) and deprenyl (a well-characterized potent inhibitor of MAO-B) were used.

Results for MAO-A activity

When the pure alkaloids isomyosmine, myosmine, anatabine, anabasine, and nornicotine were compared, isomyosmine was the most potent of the five in inhibiting the enzymatic activity of MAO-A (FIG. 1). The way to read this line graph is the following: a 100% activity means that the test compound has no effect on the enzyme; a 0% activity means that the test compound completely kills the enzyme. The more the curve is shifted to the left, the greater the inhibition the test compound exerts on the enzyme. As can be seen in FIG. 1, the curve for isomyosmine is more shifted to the left among the five alkaloids tested. A 2 mM concentration (2,000 micromolar) gives an inhibition of about 50%. The curve for clorgyline, the positive control for the experiment, is greatly shifted leftward.

Results for MAO-B activity

Figure 2:
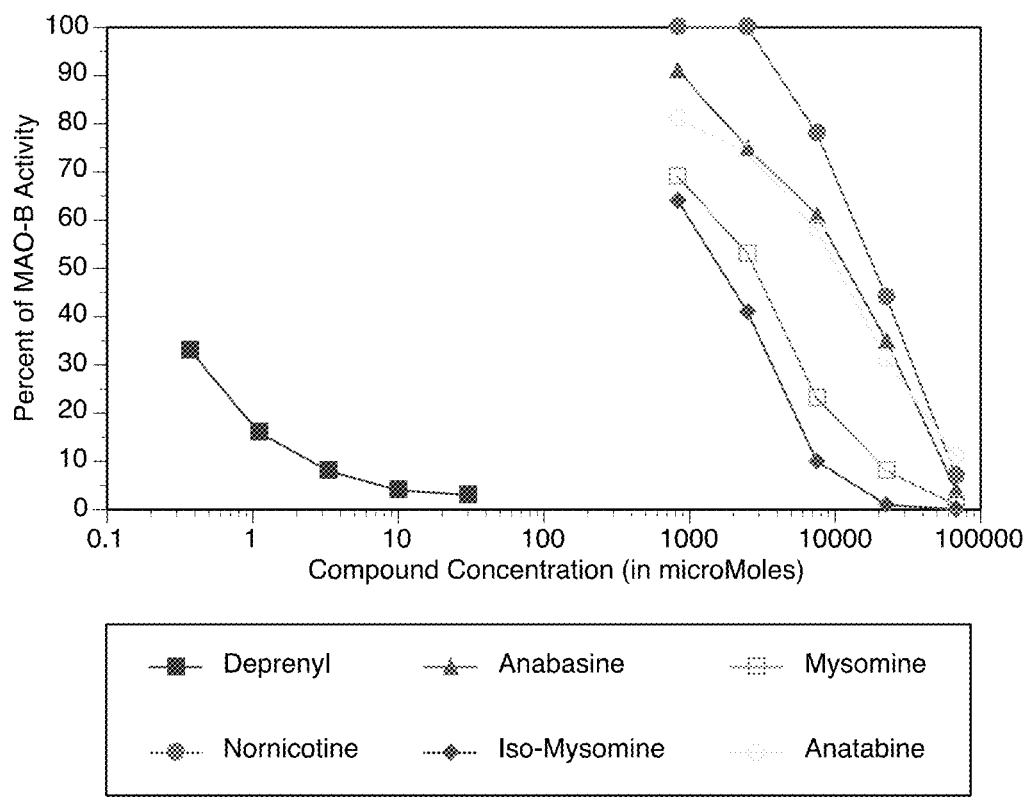
FIG. 2 is a graph showing the ability of isomyosmine, myosmine, anatabine, anabasine, and nomicotine to inhibit the activity of MAO-B.

Similar results were obtained when testing the five pure alkaloids isomyosmine, myosmine, anatabine, anabasine, and nornicotine for the inhibition of MAO-B. Isomyosmine was the most potent among the five alkaloids tested at inhibiting the activity of MAO-B (FIG. 2).

Example 2

This example illustrates treating a stage-four cancer patient who had been diagnosed with autoimmune amyloidosis. At the time treatment began, the individual was bedridden under hospice care and told he had only a few days to live. The individual was administered a daily dose of 250 mg isomyosmine. Within two weeks of treatment, the individual's symptoms had remarkably improved and the individual was able to get out of bed and walk around.

The patient's blood was tested using conventional immunoglobulin light chain Kappa/Lambda detection. The immunoglobulin kappa and lambda (Ig κ/λ) in situ hybridization (ISH) system is designed for the detection of human kappa and lambda immunoglobulin light chain messenger RNA (mRNA) in tissue sections and blood and bone marrow smears. The system uses biotin-labeled oligonucleotide probes. The probe-mRNA duplex is indirectly detected using an enzyme-conjugated antibody targeting the biotin conjugate. For color development, a chromogenic substrate is added. Enzymatic reaction of the chromogenic substrate leads to the formation of a color precipitate that is visualized by light microscopy. Results are shown in Table 1 below.

TABLE 1

| Test standard range | Initial | 3 weeks | 9 weeks | 12 weeks | 14 weeks | 17 weeks |
|---|---|---|---|---|---|---|
| Free Light Chains Ratio 0.26 ☐1.65 | 75.38 | 55.23 | 42.83 | 29.58 | 64.33 | 28.89 |
| Kappa Light Chains 3.3 ☐19.4 mg/L | 490.0 | 602.0 | 394.0 | 210.0 | 193.0 | 104.0 |
| Lambda Light Chains 5.7 ☐26.3 mg/L | 6.5 | 10.9 | 9.2 | 7.1 | 3.0 | 3.6 |

Example 3

This example illustrates administering isomyosmine to treat herpes labialis (cold sores), a type of herpes simplex occurring on the lip. An individual who experiences periodic outbreaks of herpes labialis was administered a 100 mg dose of isomyosmine upon first feeling the onset of a cold sore. The treatment was effective to prevent the outbreak of the cold sore.

Example 4

This example illustrates administering isomyosmine to treat high blood pressure. Twelve individuals experiencing high blood pressure were each administered isomyosmine at dose of 100 mg per day. Each of the individuals experienced a reduction in blood pressure during the course of treatment. The blood pressure of one of the individuals was measured to be 145/86 mmHg without isomyosmine in the bloodstream and was measured to be 109/59 mmHg while being treated with isomyosmine. Another of the individuals was being treated for type II diabetes at the beginning of the treatment. Following three months of treatment, the individual showed no symptoms of diabetes and was taken off his existing diabetes medication.

While particular embodiments have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method of treating a viral infection comprising administering to an individual in need thereof a pharmaceutical composition containing a therapeutically effective amount of isomyosmine or a pharmaceutically acceptable salt thereof.

2. The method of claim 1, wherein the viral infection is human immunodeficiency virus (HIV).

3. The method of claim 1, wherein the viral infection is human papillomavirus (HPV).

4. The method of claim 1, wherein the viral infection is herpes simplex virus (HSV).

5. The method of claim 1, wherein the therapeutically effective amount is from about 0.01 to about 50 mg/kg/day.

6. The method of claim 1, wherein the therapeutically effective amount is from about 0.1 to about 25 mg/kg/day.

7. The method of claim 1, wherein the therapeutically effective amount is from about 1 to about 10 mg/kg/day.

8. The method of claim 1, wherein the pharmaceutically acceptable salt is isomyosmine hydrochloride.

9. A method of treating influenza comprising administering to an individual in need thereof a pharmaceutical composition containing a therapeutically effective amount of isomyosmine or a pharmaceutically acceptable salt thereof.

10. The method of claim 9, wherein the therapeutically effective amount is from about 0.01 to about 50 mg/kg/day.

11. The method of claim 9, wherein the therapeutically effective amount is from about 0.1 to about 25 mg/kg/day.

12. The method of claim 9, wherein the therapeutically effective amount is from about 1 to about 10 mg/kg/day.

13. The method of claim 9, wherein the pharmaceutically acceptable salt is isomyosmine hydrochloride.

14. A method of inhibiting reactive oxygen species (ROS) in an individual suffering from a viral infection comprising administering to the individual a pharmaceutical composition containing a therapeutically effective amount of isomyosmine or a pharmaceutically acceptable salt thereof.

15. The method of claim 14, wherein the viral infection is influenza.

16. The method of claim 14, wherein the viral infection is human immunodeficiency virus (HIV).

17. The method of claim 14, wherein the viral infection is herpes simplex virus (HSV).

18. The method of claim 14, wherein the viral infection is human papillomavirus (HPV).

19. The method of claim 18, wherein the viral infection is HPV-16.

20. The method of claim 18, wherein the viral infection is HPV-18 or HPV-31.

* * * * *